United States Patent [19]

Kirkup et al.

[11] Patent Number: 4,806,637
[45] Date of Patent: Feb. 21, 1989

[54] 6-(HYDROXYETHYL)-2-(HETEROCYCLYL-THIO)-PENEM-3-CARBOXYLATES

[75] Inventors: Michael P. Kirkup, Somerset, N.J.; Amy S. Boland, Pittsburgh, Pa.

[73] Assignee: Schering Corporation, Kenilworth, N.J.

[21] Appl. No.: 840,305

[22] Filed: Mar. 17, 1986

[51] Int. Cl.[4] .................. C07D 499/00; A61K 31/425
[52] U.S. Cl. .................................................. 540/310
[58] Field of Search ............... 540/310, 350; 514/192, 514/195

[56] References Cited

U.S. PATENT DOCUMENTS

| | | | |
|---|---|---|---|
| 4,301,074 | 11/1981 | Christensen et al. | 260/245.2 R |
| 4,517,124 | 5/1985 | Broom | 260/245.2 R |
| 4,530,793 | 7/1985 | Girijavallabhan et al. | 260/245.2 R |
| 4,584,133 | 4/1986 | Girijavallabhan et al. | 260/245.2 R |
| 4,619,924 | 10/1986 | Hamanaka | 540/310 |
| 4,650,794 | 3/1987 | Christensen et al. | 540/333 |
| 4,675,317 | 6/1987 | Dininno et al. | 540/310 |

FOREIGN PATENT DOCUMENTS 126587A  11/1984  European Pat. Off. .
2013674  8/1979  United Kingdom .

Primary Examiner—Nicholas S. Rizzo
Attorney, Agent, or Firm—Gerald S. Rosen; Thomas D. Hoffman

[57] ABSTRACT

There is disclosed antibacterial compounds represented by the formula

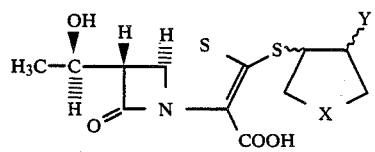

and pharmaceutically acceptable salts or pharmaceutically acceptable esters thereof,
wherein:
X represents oxygen, sulfur,

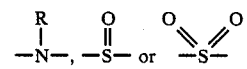

wherein R is hydrogen, loweralkyl, acetate or methoxycarbonyl;
Y is cis, trans or mixtures thereof and is selected from hydroxy, lower alkoxy, aminocarbamoyloxy, methoxycarbonylamino, lower alkylcarbonyloxy, lower alkylcarbonylamino and loweralkylsulfonylamino; and
the wavy lines indicate cis, trans or mixtures thereof.

29 Claims, No Drawings

6-(HYDROXYETHYL)-2-(HETEROCYCLYLTHIO)-PENEM-3-CARBOXYLATES

BACKGROUND

This invention relates to certain penems substituted at the 2-position by a heterocyclylthio group, their pharmaceutically acceptable salts and pharmaceutically acceptable esters, which compounds possess potent antibacterial activity and have high serum half-lives.

There is a continuing need for new antibacterial agents because continued extensive use of effective antibacterials gives rise to resistant strains of pathogens.

Antibacterials of the penem-type are known in the art. U.S. Pat. No. 4,272,437 discloses a large number of penems including those with a 6-(1-hydroxyethyl) substituent as shown e.g., in Examples 41, 58, 60, 61, 62, 63, 64, 65, 66 and 96. Examples 64 and 65 disclose penems with the 5R,6S stereochemical structure. There are no disclosures in the patent of penems with a heterocyclylthio at the 2-position.

U.S. Pat. No. 4,301,074 discloses penems with an —SR substituent at the 2-position. The R can be a 5-member heterocyclic group, but not a saturated heterocyclic group.

British Pat. No. 2,013,674A discloses penems with a hydroxyethyl group at the 6-position, but no saturated 5-membered heterocyclylthio groups at the 2-position.

SUMMARY OF THE INVENTION

This invention relates to certain novel cis and trans isomers of 5R,6S,8R 6-(1-hydroxyethyl)-2-(heterocyclylthio)-penem-3-carboxylates which possess antibacterial activity, pharmaceutical compositions thereof and methods for treating bacterial infections utilizing said compounds and compositions.

More particularly, this invention relates to compounds represented by the following formula I

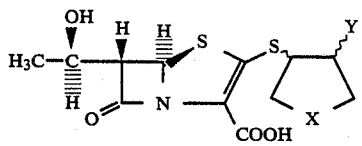

and pharmaceutically acceptable salts or pharmaceutically acceptable esters thereof,
wherein
X represents oxygen,

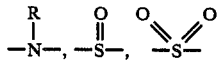

or sulfur, wherein R is hydrogen, lower alkyl, acetate or methoxycarbonyl;

Y is cis, trans or mixtures thereof and is selected from hydroxy, lower alkoxy, aminocarbamoyloxy, methoxy-carbonylamino, lower alkyl carbonyloxy, lower alkylcarbonylamino and lower alkyl sulfonylamino; and the wavy lines indicate cis, trans or mixtures thereof.

As used herein, "lower alkyl" when used alone or in combination with another moiety means straight and branched chain alkyl groups having from 1 to 6 carbon atoms, e.g. methyl, ethyl, n-propyl, iso-propyl, butyl, t-butyl, pentyl, hexyl and the like.

The heterocyclic radicals at the 2-position include for examples, tetrahydro-3-hydroxy-4-furanyl, 3-hydroxy-4-pyrrolidinyl, tetrahydro-3-amino-4-furanyl, tetrahydro-3-methoxycarbonylamino-4-furanyl, tetrahydro-3-acetoxy-4-furanyl, tetrahydro-3-methoxy-4-furanyl, tetrahydro-3-carbamoyloxy-4-furanyl, 1-acetyl-3-hydroxy-4-pyrrolidinyl, tetrahydro-3-hydroxy-1,1-dioxothiophene-4-yl, and the like.

"Pharmaceutically acceptable salts" as used herein means alkali metal salts such as sodium and potassium salts; alkaline earth metal salts such as calcium, magnesium and aluminum salts; amine salts formed from a wide variety of suitable organic amines, i.e., aliphatic, cycloaliphatic, (cycloaliphatic)aliphatic or araliphatic primary, secondary or tertiary mono-, di- or polyamines, or heterocyclic bases, e.g., salts derived from triethylamine, 2-hydroxyethylamine, di-(2-hydroxyethyl)amine, tri-(2-hydroxyethyl)amine, 4-aminobenzoic acid-2-diethylaminoethyl ester, 1-ethylpiperidine, bicyclohexylamine, N,N'-dibenzylethylenediamine, pyridine, collidine, quinoline, procaine, dibenzylamine, 1-ephenamine and N-alkylpiperdine. Acid addition salts formed from mineral acids such as hydrochloric, hydrobromic, hydroiodic, phosphoric or sulfuric acids, or formed from organic carboxylic or sulfonic acids such as trifluoroacetic, para-toluene sulfonic, maleic, acetic, citric, oxalic, succinic, benzoic, tartaric, fumaric, mandelic, ascorbic acid and malic acids. The compounds of this invention which contain a 3-carboxylic group and a basic group (the nitrogen containing heterocyclic group) form an inner salt, i.e., a Zwitterion.

"Pharmaceutically acceptable esters" means physiologically cleavable esters, i.e., metabolizable esters known in the penicillin, cephalosporin and penem arts to be easily cleaved within the body to the parent acid. Examples of such esters are indanyl, phthalidyl, methoxymethyl, glycyloxymethyl, phenylglycyloxymethyl, thienylglycyloxymethyl, acetoxymethyl and pivaloyloxymethyl.

Preparation of the foregoing salts and esters may be carried out according to conventional procedures for forming salts of beta-lactams such as penicillins, cephalosporins and penems. Salts can be formed, for example, by treating with metal compounds such as alkali metal salts of suitable carboxylic acids, or with ammonia or a suitable organic amine, wherein preferably stoichiometric amounts or only a small-excess of the salt-forming agent is used. Acid addition salts are obtained in the usual manner, for example, by treating with an acid or a suitable anion exchange reagent. Inner salts of the compounds of formula I, i.e., a Zwitterion, may be formed by neutralizing salts such as acid addition salts to the isoelectric point. The esters are preparable in a manner analogous to the preparation of the corresponding esters of penicillins and cephalosporins.

Salts may be converted in the usual manner into the free carboxy compounds.

"Inert organic solvent" means an organic solvent which is unreactive at the reaction conditions, typical suitable solvents used in the processes for making compounds of formula I are tetrahydrofuran (THF), methylene chloride, diethylether, dimethylformamide (DMF), a lower alkanol such as methanol, pyridine, acetonitrile and the like.

The compounds of this invention possess 3 or more asymmetric carbon atoms indicated in formula Ia below at the 5, 6, and 8 and the 3' and 4' position carbon atoms on the heterocyclic substituent.

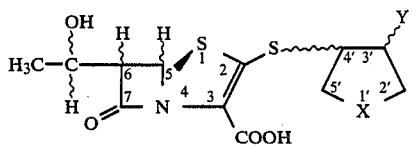

wherein X is

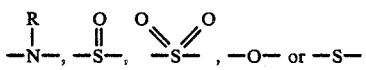

and Y is as defined in formula I.

The absolute stereochemistry at the 5, 6 and 8 positions for the compounds of this invention is 5R, 6S, 8R and at the 3' and 4' positions the cis compounds, i.e. 3'R, 4'S and 3'S, 4'R or the trans compounds, i.e. the 3'S, 4'S and 3'R, 4'R stereoisomers.

DETAILED DESCRIPTION

When tested in standardized microbiological assays, the compounds of this invention are active against such gram-positive organisms as *Staphylococcus epidermis* and *Bacillus subtilis,* and such gram-negative organisms as *E. coli* and Salmonella at test levels of 0.06 to 1.0 micrograms/ml. Additionally, they show activity against organisms which produce beta-lactamases, e.g. penicillinase and cephalosporinase, indicating a resistance to these enzymes.

The compounds of this invention also display good serum half-lives, e.g. up to approximately 7 minutes in mice tests, and they also exhibit low protein binding. Their metabolites have little or no unpleasant odor.

The compounds of this invention are useful for treating warm-blooded animals (including humans) having a susceptible bacterial infection. The compounds can be administered orally, parenterally, transdermally and topically. In addition, the compounds can be used to sterilize materials which are contaminated by susceptible bacteria, e.g. medical and dental instruments. Thus, this invention includes within its scope pharmaceutical compositions comprising the compounds of this invention in admixture with a pharmaceutically acceptable carrier therefor. In addition, the present invention also provides a method of treating bacterial infections in animals, particularly warm-blooded animals including humans, having a susceptible bacterial infection which comprises administering to said animal an antibacterial effective amount of a compound of this invention, or a pharmaceutical composition thereof. In the foregoing compositions, the compounds of this invention can be used as the sole active antibacterial agent or in combination with other antibacterial agents and/or enzyme inhibitors.

For oral administration, the compounds of this invention are typically formulated in the form of tablets, capsules, elixirs, or the like. For parenteral administration, they may be formulated into solutions or suspensions. Typical topical formulations are those such as lotions, creams, ointments, sprays, and mechanical delivery devices, e.g., transdermal.

Typical pharmaceutically acceptable carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tri-calcium phosphate; sodium sulfate; calcium sulfate; polyvinyl pyrrolidone; polyvinyl alcohol; stearic acid; alkaline earth metal stearates such as magnesium stearate; vegetable oils such as peanut oil, cottonseed oil, sesame oil, olive oil and corn oil; non-ionic, cationic and anionic surfactants; ethylene glycol polymers; betacyclodextrin; fatty alcohols, hydrolyzed cereal solids; water; polyalkylene glycols; gums; and petroleum; as well as other non-toxic compatible fillers, binders, disintegrants and lubricants commonly used in pharmaceutical formulations. The compositions may also contain preservatives, aerosol propellants and coloring, thickening, suspending, dispensing, emulsifying, wetting, stabilizing and buffering agents.

The dosage of the compounds of this invention which is administered is dependent, in the judgment of the attending clinician, upon a variety of factors, i.e., the age and weight of the individual being treated, the mode of administration, the potency of the administered compound and the type and severity of the bacterial infection being prevented or reduced. Typically, the dosage administered per day will be in the range of from about 25 to 160 mg/kg and preferably from about 50 to 100 mg/kg in divided dosages. Typically, the dosage will be administered in dosage units containing convenient amounts, for example, 0.05, 0.100, 0.250, 0.500, 1 or 2 gms of active ingredient combined with a suitable pharmaceutically acceptable carrier or diluent.

The cis and trans stereoisomers or racemates of the compounds of Formula I can be prepared according to the reaction schemes which follow. The process used is dictated by the stereoisomer desired and the heterocyclyl substituent on the 2-position of the penem.

The preferred preparation of the trans stereoisomer wherein the substituent is a tetrahydrofuran is shown in the following Reaction Scheme I.

SCHEME I

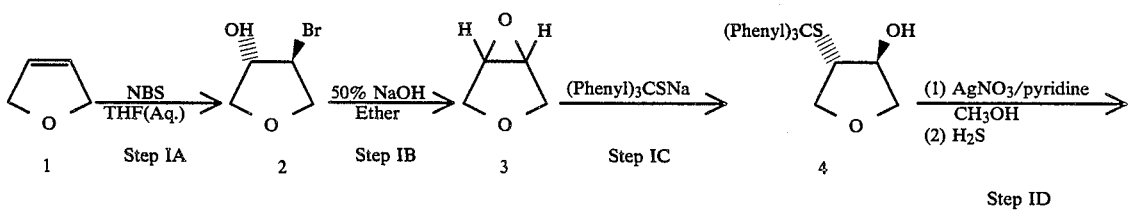

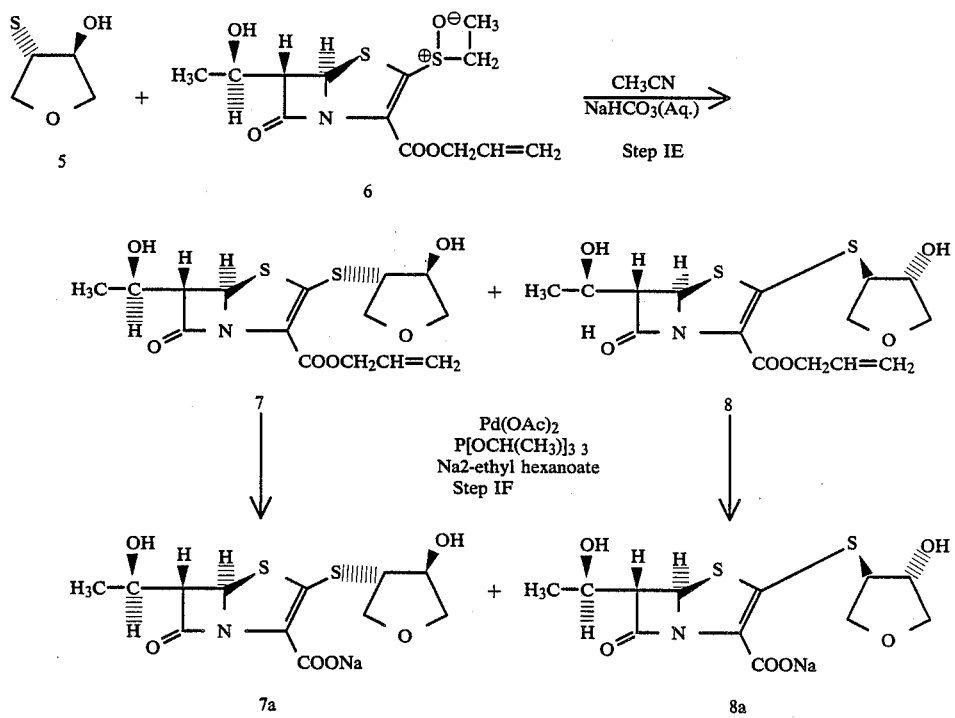

In Step IA, the reaction of 2,5 dihydrofuran and N-bromosuccinimide (NBS) is carried out in an aqueous mixture of an inert organic solvent and water at from about 20° C. to 30° C., preferably room temperature. A preferred solvent is tetrahydrofuran (THF) although other solvents such as diethylether and dimethoxyethane (DME) are also suitable. The product, compound 2, is then recovered by distillation after working up the reaction mixture with $Na_2SO_3$ to quench excess NBS, separating the organic and aqueous layers and filtering off precipitated succinimide or N-hydroxysuccinimide.

In Step IB the bromohydrin from step IA is epoxidized by reacting with an aqueous base in an inert organic solvent for about an hour at room temperature. Preferred bases are aqueous potassium or sodium hydroxides. Preferred inert organic solvents are methylene chloride or diethyl ether.

In Step IC, the epoxide produced in step IB is converted to trans 3-triphenylmethanethio-4-hydroxytetrahydrofuran by reaction with the compound produced by the reaction of sodium hydride, and triphenylmethanethiol in an inert, organic solvent at cold temperatures in an inert atmosphere. The preferred inert organic solvent is dimethylformamide (DMF), the preferred inert atmosphere is nitrogen and the preferred temperature is about −10° C. to 5° C., most preferably 0° C.

The epoxide is reacted with the above reaction product in the same solvent, under an inert atmosphere, e.g. nitrogen, at a temperature of about 20° C. to 30° C., preferably room temperature, until the reaction is complete, e.g. about one hour, Compound 4 is then recovered.

In Step ID, compound 4 in a dry inert organic solvent such as a lower alkanol, e.g. methanol substantially free of water, is reacted with silver nitrate in the same inert organic solvent containing an organic base, e.g., triethylamine or pyridine. This causes the silver salt of compound 5 to precipitate. The reaction is conducted at room temperature for about 30 minutes.

The precipitate is recovered and suspended in a suitable inert organic solvent, e.g. acetonitrile, and treated with hydrogen sulfide gas for about 10-15 minutes to remove the silver as silver sulfide. Compound 5, in solution, is then recovered and used in the subsequent reaction with compound 6 without further purification. Although compound 5 can be isolated, it is not necessary when using it to produce penems.

In Step IE, compound 5 in the solution recovered in Step ID is reacted with compound 6 in the presence of aqueous sodium bicarbonate until the reaction is complete, usually about 30 minutes to yield compounds 7 and 8, one as a precipitate and the other as an oil. Compound 6 is prepared by known methods, e.g. as described in European Patent Application No. 0046363, published Feb. 24, 1982, pages 13, 14 and 15.

The allyl protecting group of compounds 7 and 8 are removed by known methods, e.g. as described in U.S. Pat. No. 4,314,942 wherein 2-ethylhexanoic acid or an alkali metal salt thereof and a catalytic amount of an organic soluble palladium complex effects removal of the protecting group. The resulting products 7a and 8a respectively are produced. For purposes of this invention it is preferred to use the sodium salt of 2-ethylhexanoic acid and palladium acetate in Steps IF and IG. The resulting penem products are the sodium salts which can be converted to the corresponding acid by conventional means.

The preferred preparation of the cis stereoisomer wherein the $R_1$ substituent is a tetrahydrofuran is shown in the following Reaction Scheme II.

SCHEME II

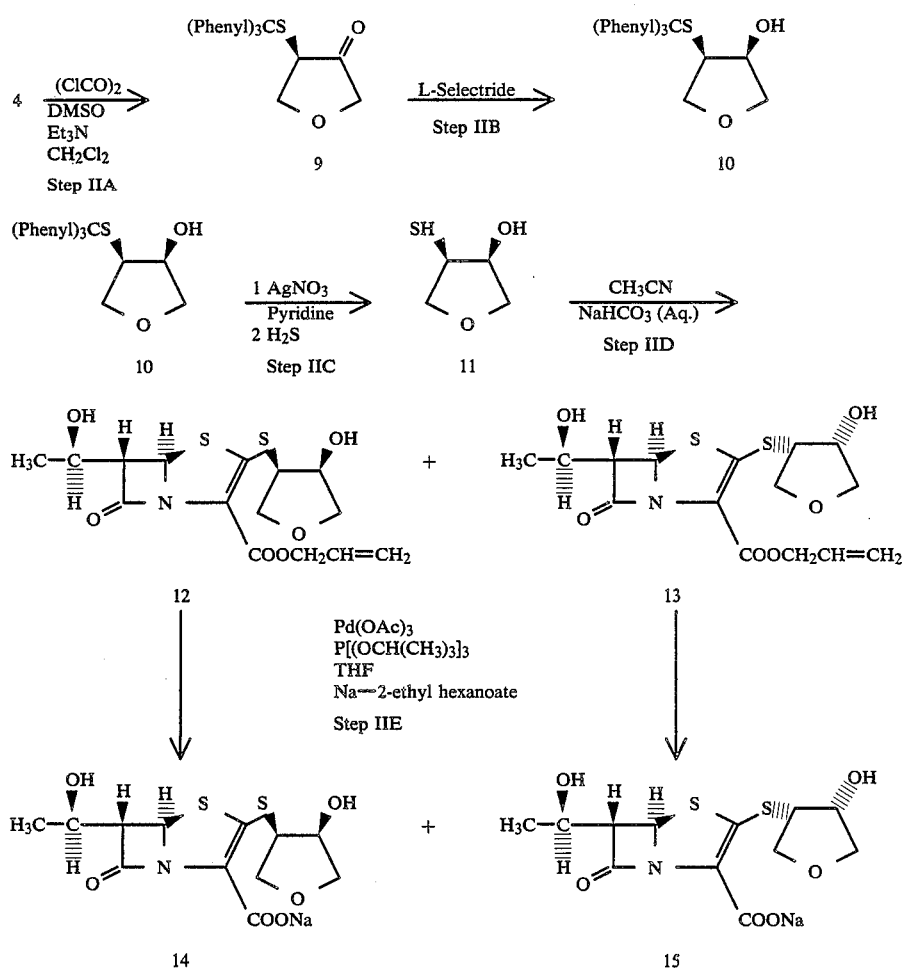

In Step IIA, compound 4 is reacted with the reactive intermediate generated from the addition of dimethylsulfoxide (DMSO) to a cold (−50° C.) solution of oxalyl chloride in an inert organic solvent, e.g. methylene chloride. When the reaction mixture warms to about −35° C., a trisubstituted organic base, e.g., triethylamine, is added in the same inert organic solvent. After the reaction is complete the solvent is removed and the product, compound 9, is recovered.

In Step IIB, the oxo group of compound 9 is reduced to the hydroxy group by reaction with lithium tri secondary butyl borohydride in an inert atmosphere, preferably nitrogen. After completion of the reaction, the product, the cis isomer (compound 10), is recovered.

In Step IIC, compound 10 in a lower alkanol solvent, e.g. methanol, is treated with silver nitrate and pyridine in the same solvent to precipitate silver-(3-hydroxy)-tetrahydrofuran-4-thiolate. After removing the solvent the silver thiolate suspended in an inert organic solvent, e.g. acetonitrile, is treated with anhydrous hydrogen sulfide gas. When the resulting black silver sulfide ceases precipitating the reaction is complete. Compound 11 is then recovered and dissolved in an inert organic solvent, e.g. acetonitrile, for use in the next step of the process.

In Step IID, compound 6 in the same inert organic solvent used in the last part of Step IIC, is added to a cold, i.e. −10° C. to +5° C., aqueous solution of sodium bicarbonate and compound 11 in the same inert organic solvent. The reaction is conducted under an inert atmosphere, e.g. nitrogen, for about ½ hour to obtain a mixture of compounds 12 and 13 which mixture is separated into the isomers by crystallization from ethyl acetate. The first crop of crystals is one diastereomer and the second crop is the other diastereomer. The mother liquor also contains the second diastereomer.

In Step IIE, the allyl protecting groups are removed from compounds 12 and 13 by the method of U.S. Pat. No. 4,314,942, i.e. treatment with palladium acetate, triisopropyl phosphite and sodium-2-ethyl hexanoate, to obtain from compounds 12 and 13, respectively, compounds 14 and 15.

The process of Reaction Scheme II is also suitable for producing compounds of formula I wherein X is

This is accomplished by using appropriately substituted pyrrolidines in place of tetrahydrofuran in the reaction.

The preferred preparation of the trans stereoisomer wherein the heterocyclyl substituent of formula I is an amino substituted tetrahydrofuran is shown in the following Reaction Scheme III.

SCHEME III

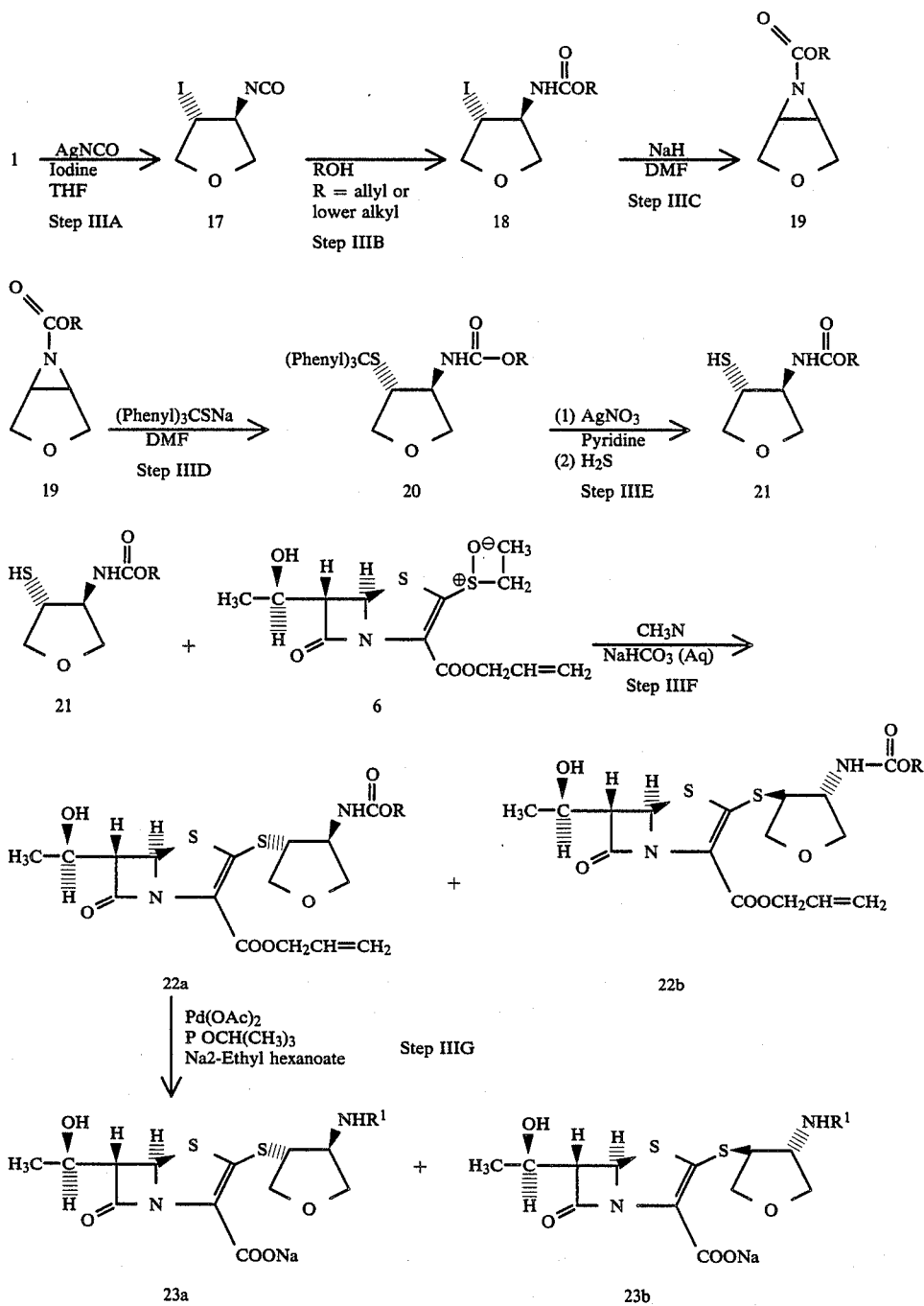

$R^1$ is hydrogen or —COO lower alkyl

In Step IIIA, compound 1 is converted to compound 16 by means known in the art, i.e. by the procedure disclosed in Hassner et al., J. Org. Chem. 32, 540 (1967). Hassner et al. involves reacting compound 1 in an inert organic solvent, e.g. tetrahydrofuran (THF), with a suspension of silver cyanate in THF which has been previously treated with iodine under an inert atmosphere, e.g. nitrogen, at a cold temperature, i.e. about −20° C. to 0° C., preferably about −10° C. After removing the silver salts and warming to room temperature (about 25° C.), compound 17 is obtained. It is not isolated but is used in situ in the next step of the process.

In Step IIIB, allyl alcohol or a lower alkanol is added to the reaction mixture resulting from step IIIA and allowed to react at room temperature in the dark under an inert atmosphere until the reaction is complete. The product, compound 18, is then recovered.

In Step IIIC, compound 18 in an inert organic solvent, e.g. DMF, is reacted with sodium hydride suspended in the same solvent under an inert atmosphere, e.g. nitrogen, at about −10° C. to 5° C., preferably about 0° C., until the reaction is complete as evidenced by thin layer chromatography (TLC) of the reaction mixture. The product, compound 19, is recovered.

In Step IIID, compound 19 is converted to compound 20 by reaction with sodium triphenylmethylthiolate in an inert organic solvent, e.g. DMF, under an inert atmosphere, e.g. nitrogen, until the reaction is complete, about 2 to 3 hours, and the product, compound 20, is recovered.

In Step IIIE, compound 20 is converted to compound 21 by reaction with silver nitrate in an alkanolic solvent, e.g., methanol containing an organic base, e.g., triethylamine or pyridine. The silver is removed by reacting the resulting silver salt with hydrogen sulfide gas in acetonitrile. The product, compound 21, which results is concentrated to remove excess H₂S gas and used in the next step without further purification.

In Step IIIF, compound 21, in the solvent from Step IIIE, is reacted with compound 6 under the conditions illustrated in Reaction Schemes I and II, Steps IE and IID, respectively, to produce compounds 22a and 22b as a mixture of side chain trans diastereoisomers.

In Step IIIG, the allyl protecting group is removed from the carboxyl at position 3 of compounds 22a and, 22b and, if that protecting group is present at position 3' of the side chain, by reaction with palladium acetate and triisopropylphosphite followed by 2-ethyl hexanoic acid to yield a mixture of compounds 23a and 23b.

The preferred preparation of the side chain cis stereoisomer wherein the heterocyclyl substituent of formula I is an amino substituted tetrahydrofuran is shown in the following Reaction Scheme IV.

SCHEME IV

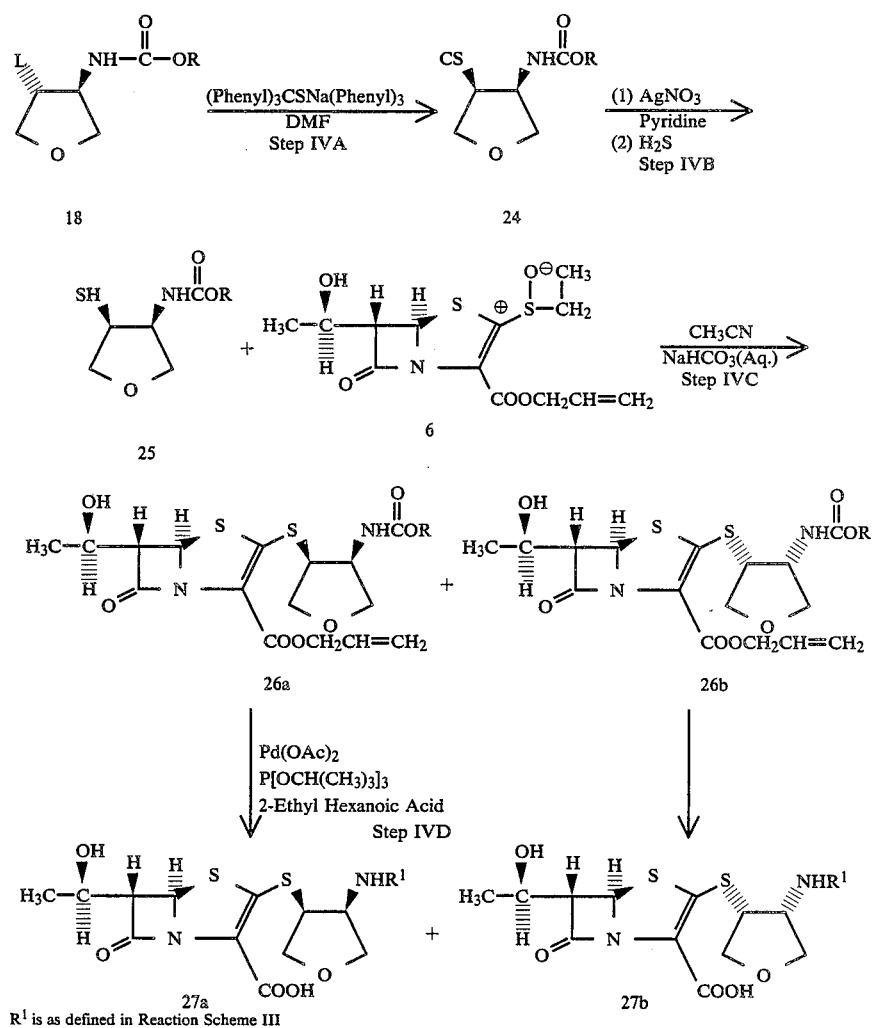

R¹ is as defined in Reaction Scheme III

In Step IVA, compound 18 (prepared as shown in Reaction Scheme III) is converted to compound 24 by reaction with sodium tritylthiolate, e.g., the compound produced when reacting sodium hydride with triphenylmethylthiol in an inert organic solvent at cold temperatures in an inert atmosphere as described in Step IC of Reaction Scheme I.

In Step IVB, compound 24 is reacted with silver nitrate in pyridine followed by H₂S under conditions as described in Reaction Scheme II, Step IIC, to yield compound 25 which is not isolated but remains in the reaction mixture for use in the next step of the process.

In Step IVC, compound 6 is added to a cold aqueous solution of sodium bicarbonate and compound 25 under conditions described for Reaction Scheme II, Step IID, to yield a mixture of cis side chain stereoisomers, compounds 26a and 26b.

In Step IVD, compounds 26a and 26b are deprotected by removing the allyl groups at the carboxyl and amino substituents as described for Reaction Scheme III Step G, to yield a mixture of cis side chain stereoisomers, compounds 27a and 27b.

The preferred preparation of the side chain trans stereoisomers wherein the $R^1$ 2-heterocyclic substituent of formula I is an hydroxy substituted pyrrolidine is shown in the following Reaction Scheme V.

SCHEME V meta chloroperbenzoic acid as illustrated in Step VB or by converting compound 29 to the bromohydrin (compound 30) by reaction with hypobromous acid in aqueous THF as illustrated in Step VC, then epoxidizing in a basic medium, e.g. 50% KOH in methylene chloride to yield compound 31, as illustrated in Step VD. The

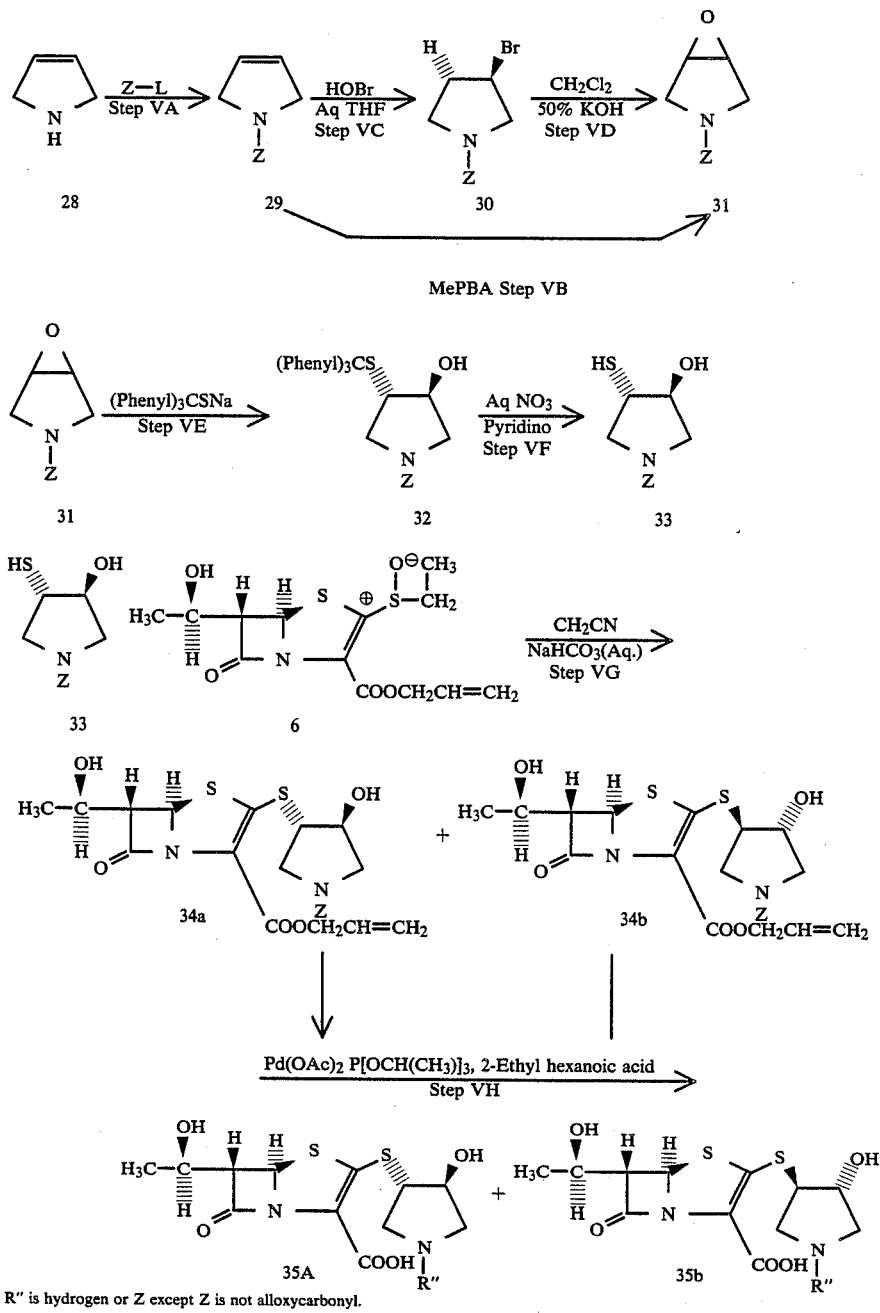

R" is hydrogen or Z except Z is not alloxycarbonyl.

In Step VA, the nitrogen on the pyrrole (compound 28) is protected with an acyl protecting group, e.g. allyloxycarbonyl, by reaction with a compound of the formula Z-L wherein Z is an acyl group, e.g. allyloxycarbonyl, acetyloxycarbonyl or benzyloxycarbonyl and L is a leaving group such as a halogen, e.g., iodine, or a mixed anhydride, e.g., trimethylacetyloxy, to yield compound 29.

Compound 31 is prepared by either converting compound 29 directly to compound 31 by reaction with use of Steps VC and VD is the preferred route because it results in higher yields and is more widely applicable, whereas in Step VB when Z is allyloxycarbonyl the resulting product contains significant amounts of a diepoxide side product which must be separated.

In Step VE, compound 31 is converted to compound 32 by reaction with sodium triphenylmethylthiolate in an inert organic solvent, e.g. DMF, under an inert atmosphere, e.g. nitrogen, until the reaction is complete.

In Step VF, compound 32 is converted to compound 33 by reaction with silver nitrate in pyridine under conditions as described in Reaction Scheme III Step IIIE.

In Step VG, compound 33 is reacted with compound 6 in the presence of acetonitrile and aqueous $NaHCO_3$ to yield a mixture of compound 34a and 34b.

The protecting allyl groups are removed from the carboxyl, and the nitrogen, if present, as shown in Step VH by reaction with palladium acetate and triisopropylphosphite followed by 2-ethyl hexanoic acid to yield a mixture of compounds 35a and 35b.

In cases where the group on the nitrogen is not allyloxycarbonyl, the substituent remains and only the allyl on the carboxyl group is removed leaving a hydrogen.

The following illustrates the preparation of compounds and compositions of this invention.

EXAMPLE 1 d,l-trans-3-bromo-4-hydroxytetrahydrofuran

To a solution of 2,5-dihydrofuran (10.0 gm) in $THF/H_2O$ (175 mL THF, 20 ml $H_2O$) add N-bromo succinimide (26.5 gm). Keep the reaction mixture at room temperature overnight. Then add 50 mL of 10% $Na_2SO_3$ and stir the mixture for ½ hr. Separate the layers by addition of 50 mL water and 50 mL brine. Extract the aqueous layer with ethyl acetate (EtOAc) (3×75 mL). Combine the organic layers, wash with brine (1×100 mL), dry ($MgSO_4$) and remove the solvent by vacuum distillation. Remove precipitated succinimide by filtration (washed with $Et_2O$) and distill the product under vacuum (90° C., 10 mmHg) yielding pure title compound. +H'NMR ($CDCl_3$): $\delta$ 3.2–4.7 ($\delta$, multiplet, $D_2O$ exchange removes absorption at $\delta$ 3.5)

EXAMPLE 2

2,5-dihydrofuranoxide

Dissolve the bromohydrin from Example 1 (6.485 g) in 60 mL diethylether ($Et_2O$) and add 10.5 mL of 50% NaOH (aq). Stir the resulting biphasic mixture rapidly at room temperature for 1 hr. to separate the Layers and extract the aqueous phase with diethylether ($Et_2O$) (1×40 mL). Combine the ether layers and extract with brine (15 mL), dry ($MgSO_4$) and remove the ether by distillation at atmospheric pressure to yield the title compound:

H'NMR ($CDCl_3$): $\delta$ 4.03 (d, 2, J=10 $H_z$), 3.76 (s, 2), 3.61 (d, 2, J=10 $H_z$).

EXAMPLE 3 d,l-trans-3-triphenylmethylthio-4-hydroxytetrahydrofuran

To a suspension of sodium hydride (0.18 gm) in DMF (15 mL) add a solution of triphenylmethylthiol (2.07 gm in 5 mL DMF). Cool the mixture to 0° C. and allow to stir for ½ hr. under $N_2$ atmosphere. Add a solution of the epoxide from Example 2 (0.624 g in 2 mL DMF) and continue stirring for an additional hour at room temperature. Add Water (20 mL) and extract the mixture with ethylacetate (EtOAc) (2×25 mL). Wash the organic layer with brine (1×20 mL), dry ($MgSO_4$) and remove the solvent under vacuum. Purify the title compound by silica gel chromatography (10% acetone/$CH_2Cl_2$) to yield pure title compound.

H'NMR ($CDCl_3$)

EXAMPLE 4 d,l-trans-3-mercapto-4-hydroxytetrahydrofuran

To a solution of the alcohol from Example 3 (4.21 gm) in dry methanol (50 mL) add a solution of silver nitrate (1.98 gm) in 15 mL of methanol:pyridine (15:1). The solution becomes cloudy and precipitation of the silver salt of the title compound occurs over the course of 5–10 min. After 30 min., remove methanol by vacuum distillation and keep the residue under high vacuum for 1 hr. Suspend the resulting gummy residue in acetonitrile (50 mL) and bubble $H_2S$ gas through the mixture with stirring for 5–10 min. until all of the gummy silver salt reacts leaving a colorless solution of the title compound and a black precipitate of silver sulfide. Bubble nitrogen gas through the reaction mixture for 1 hr. to remove hydrogen sulfide gas. Remove the silver sulfide by filtration through Celite. Reduce the volume of solvent to 30 mL by vacuum distillation and use the resulting solution of the title compound in the following step without further purification.

EXAMPLE 5 allyl-(5R,6S,8R)-6-(1-hydroxyethyl)-2-[tetrahydro-3'S-hydroxy-4'S-furanyl)thio]-penem-3-carboxylate and allyl-(5R,6S,8R)-6-(1-hydroxyethyl)-2-[(tetrahydro-3'R-hydroxy-4'R-furanyl)thio]-penem-3-carboxylate)

To the solution prepared in Example 4 (in acetonitrile) add a solution of $NaHCO_3$ (2.5 gms) in 25 mL of water followed by 1.94 gm of the penem sulfoxide identified as compound 6 in Reaction Scheme I in 10 mL of acetonitrile. After 30 min. the reaction is complete. Partition the mixture between ethylacetate (50 mL) and water (50 mL). Dry the organic layer ($MgSO_4$) and concentrate to a volume of about 25 mL by vacuum distillation. Precipitation of one of the title diastereoisomers occurs during this step, collect the precipitate by filtration. Wash the filtrate with cold ethylacetate and dry the crystalline material under vacuum to yield one diastereoisomer. Concentrate the combined filtrates to yield a second crop of crystals and treat in the same manner as the first crop. Concentrate the filtrate to an oil and purify by silica gel chromatography (15% acetone/$CH_2Cl_2$) to give a second pure diastereoisomer.

H'NMR of the first diastereoisomer ($CDCl_3$): $\delta$ 6.2–5.7 (m, 1H), 5.79 (d, 1H, J=2 $H_z$), 5.48 (m, 1H), 5.25 (m, 1H), 4.80 (d, 1H, J=5 Hz), 4.60 (m, 2H), 4.4–3.4 (complex multiplet, 10H), 2.8 (singlet, 1H, exchangeable with $D_2O$), 1.22 (d, 3H, J=6 Hz).

The following trans compounds of this invention can be made following the procedures of Examples 1–5, but after Example 3 the hydroxy group is derivatized as shown in Table I:

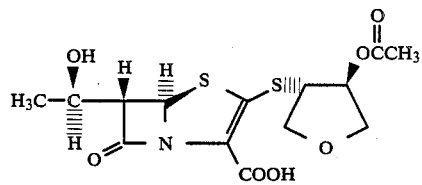

1.

-continued

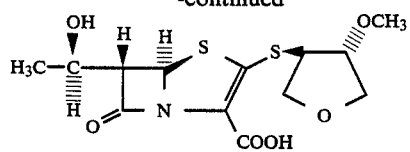

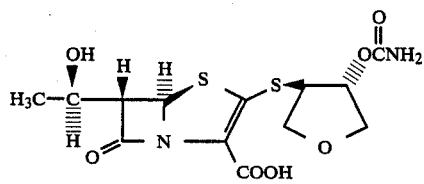

and purify the product by silica gel chromatography (100% CH₂Cl₂) to obtain the title compound.

H'NMR (CDCl₃): δ 3.1-4.1 (m, 5H), δ 6.9-7.7 (m, 15H).

EXAMPLE 7 d,l-cis-3-tritylthio-4-hydroxytetrahydrofuran

To a solution of purified ketone prepared in Example 6 (1.54 gms) in 15 mL of dry THF, cooled to −10° C., add 5.13 mL of 1M L-selectride (Aldrich Chemical Co.) via syringe and allow the reaction to proceed for 1 hr. at ambient temperature under N₂ atmosphere. Quench the reaction with 5 mL 10% NaOH (aq) and allow to react for 30 min. Partition the reaction mixture between ethylacetate (30 mL) and water (30 mL). Wash the

TABLE 1

| Starting Compound | Reaction | Product |
|---|---|---|
| 1. | acetylchloride inert organic solvent triethylamine | |
| 2. | CH₃I inert organic solvent organic base | |
| 3. | sodium isocynate strong organic acid, e.g., trifluoroacetic acid | |

Then the procedures of Examples 4 and 5 are followed.

EXAMPLE 6

3-keto-4-tritylthiotetrahydrofuran

Cool a solution of oxalyl chloride (1 mL) in 20 mL CH₂Cl₂ to −50° C. Add a solution of DMSO (1.38 mL) in 20 mL CH₂Cl₂ over the course of 2-3 min. via a pressure equialized addition funnel. Keep the temperature below −40° C. and stir for 10 min., then add a solution of the alcohol prepared in Example 3 in 15 mL CH₂Cl₂ and remove from the ice bath. Allow to warm to −35° C. and add a solution of triethylamine in 20 mL CH₂Cl₂. The mixture will warm to about +10° C. then add 20 mL 10% aq. tartaric acid, stir for 5 min., add 20 mL of brine, 50 mL of water and extract organic layer. Wash CH₂Cl₂ layer with water (1×100 mL) and dry (MgSO₄). Remove the solvent via vacuum distillation organic layer with 5% tartaric acid (aq) and dry (MgSO₄). Remove the solvent by vacuum distillation and purify on silica gel (5%) Et₂O/hexane→7% Et₂O/hexane) to obtain the title compound as a pure cis isomer.

H'NMR (CDCl₃): δ 2.75–3.2 (m, 2H), δ 3.35–3.70 (m, 1H), 3.71 (d, 1H), J=1.5 Hz) 4.00 (sextet, 2H, J=4 Hz), 7.0–7.76 (m, 15H).

EXAMPLE 8 allyl-(5R,6S,8R)-6-(1-hydroxyethyl)-2-[(tetrahydro-3'S-hydroxy-4'R-furanyl)thio]-penem-3-carboxylate and allyl-(5R,6S,8R)-6-(1-hydroxyethyl)-2-[(tetrahydro-3'R)-hydroxy-4'S-furanyl)thio]-penem-3-carboxylate)

Dissolve the s-trityl alcohol from Example 7 (3.21 g) in methanol and add a solution of silver nitrate (1.5 gm) and pyridine (0.80 mL) in methanol (10 mL). Silver-(3- hydroxy)tetrahydrofuran-4-thiolate precipitates from solution as a gum. Decant methanol when the reaction is complete (15 min.), and place the reaction flask under high vacuum for 1 hour. Then suspend the silver thiolate in acetonitrine (50 mL) and bubble anhydrous hydrogen sulfide gas through the reaction mixture until precipitation of black silver sulfide ceases (1–2 min.). Remove the silver salts by filtration through celite and remove the solvent by distillation (atmospheric). Redissolve the residue (3-hydroxy-4-mercapto-tetrahydrofuran) in fresh acetonitrile. Add an aqueous solution of sodium bicarbonate (2.9 gm in 50 mL water) to the cold (0° C.) acetonitrile solution of 3-hydroxy-4-mercapto-tetrahydrofuran followed by addition of the penem sulfoxide (compound 6) (1.5 gm) in acetonitrile (10 mL). The reaction is complete after 30 min. of rapid stirring under an atmosphere of nitrogen. Partition the biphasic mixture between ethylacetate and water (50 mL each) and dry the organic phase (MgSO$_4$). Remove the solvent by vacuum distillation then recrystallize from ethyl acetate to give 2 crops of penem allyl ester. The first crop (1.3 gms) consist of a single diastereoisomer. The second crop and the mother liquor are predominantly the other possible diastereoisomer.

MS, M/z=373

EXAMPLE 9

Sodium-(5R,6S,8R)-6-(1-hydroxyethyl)-2-[(cis-tetrahydro-3'-hydroxy-4'-furanyl)thio]-penem-3-carboxylate To dry, oxygen free tetrahydrofuran (20 mL) add palladium acetate (0.0162 gm), followed by triisopropyl phosphite (0.150 gms) and then sodium-2-ethylhexanoate (0.240 gms). Finally add the mixture of penem allyl esters made in Example 8 and stir the reaction under nitrogen for 1 hour. Collect the resulting precipitate by centrifugation, wash the residue several times with ethyl acetate and ether, and then dry under vacuum to give a mixture of title compounds wherein the side chains are cis diastereoisomers.

The following cis compounds of this invention can be made following the procedures of Examples 6–9, but after Example 7 the hydroxy group is derivatized as shown in Table 2:

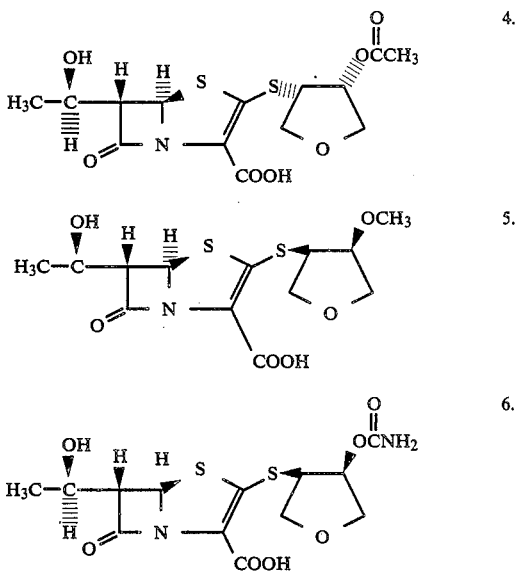

EXAMPLE 9

TABLE 2

| Starting Compound | Reaction | Product |
|---|---|---|
| 4. (trityl-S-tetrahydrofuran-OH) | acetylchloride inert organic solvent triethylamine | (trityl-S-tetrahydrofuran-OCCH$_3$) |
| 5. (trityl-S-tetrahydrofuran-OH) | CH$_3$I inert organic solvent organic base | (trityl-S-tetrahydrofuran-OCH$_3$) |

TABLE 2-continued

| Starting Compound | Reaction | Product |
|---|---|---|
| 6. Ph₃C—S—[tetrahydrofuran-OH] | sodium isocynate strong organic acid, e.g., trifluoroacetic acid | Ph₃C—S—[tetrahydrofuran-OC(O)NH₃] |

Then the procedures of Examples 8 and 9 are followed.

EXAMPLE 10 trans-3-isocyanato-4-iodo-tetrahydrofuran and trans-3-allyloxycarbonylamino-4-iodo-tetrahydrofuran Prepare the trans iodo isocyanate title compound in situ according to the procedure of Hassner et al. *J. Org. Chem.* 32, 540, (1967), and then transform to the title allyloxycarbonyl compound without isolation or purification:

To a cold (−10° C.) suspension of silver cyanate (6.07 gms) in dry THF (50 mL) add I₂ (8.5 gms) and stir the mixture vigorously under N₂ for 1 hr. Then add 2,5 dihydrofuran (2.27 mL, 2.1 gms) in 10 mL THF. Remove the mixture from the cold bath and stir at room temperature for 30 min. Remove the silver salts by filtration through Celite and keep the reaction mixture at room temperature in the dark overnight. Then add allyl alcohol (25 mL) along with 2 drops of 1M lithium methoxide/methanol and keep the mixture at room temperature overnight in the dark under nitrogen. Then partition the mixture between ethylacetate and brine (50 mL each). Wash the organic layer several times with water (25 mL), dry (MgSO₄) and concentrate to an oil (house-high vacuum). Chromatography on silica gel (100% $CH_2Cl_2 \rightarrow$ 10% EtOAc/$CH_2Cl_2$) affords the title compound.

H'NMR (CDCl₃): δ 3.6–4.8 (m, 8H), δ 5.15–5.5 (m, 2H), 5.6–6.2 (m, 24), MS (EI), M/z, 297 (M+).

EXAMPLE 11

6-allyoxycarbonyl-3-oxa-6-azabicyclo[3.1.0]hexane

Dissolve the iodo carbamate made in Example 10 (1.21 gms) in DMF (15 mL) and cool to 0° C. Add a suspension of sodium hydride (115 mgs) in DMF and the stir reaction mixture under N₂ for 1.5 hrs. TLC of the reaction mixture (15% EtOAc/$CH_2Cl_2$) showed complete conversion to a new compound of slightly higher rf. Carefully treat the mixture with dilute ammonium chloride (20 mL) and extract the product into ether (3×30 mL). Wash the organic layer was washed with brine (1×20 mL), dry (MgSO₄) and remove the solvent under vacuum to give the title compound.

M+/z: 169 H'NMR (CDCl₃): δ 3.15 (s, 2H), 3.55 (d, 2H, J=6 Hz) 4.15 (d, 2H J=6 Hz), 4.52 (d, 2H, J=4 Hz), 5.1–5.45 (m, 2H), 5.61–6.15 (M, 1H).

EXAMPLE 12 d,l-trans-3-triphenylmethylthio-4-allyloxycarbonylaminotetrahydrofuran

To a solution of triphenylmethylthiol (3.0 gms) in dMF (50 mL) add a suspension of NaH (270 mgs) in DMF (2 mL). Stir the mixture rapidly under nitrogen for two hours or until bubbling ceases. Add the resulting clear brown solution of the sodium thiolate to a solution of 1.4 gms of the aziridine made in Example 11 in 15 mL of DMF and allow the reaction to proceed with stirring under nitrogen for 2.5 hours. Then dilute the reaction mixture with 50 mL of dilute aqueous ammonium chloride and brine (50 mL). Extract the resulting product into ether (3×75 mL), dry (MgSO₄) and remove the solvent under vacuum. Chromatography on silica gel (100% $CH_2Cl_2$) gives the title compound as a crystalline product.

MS, M+/z=445 H'NMR (CDCl₃): δ 3.0–3.95 (m, 6H), 3.9–4.4 (m, 2H), 4.45–4.71 (d, 2H, J=4 Hz), 5.0–5.5 (m, 3H), 5.6–6.2 (m, 1H), 7.1–7.6 (m, 15H).

EXAMPLE 13 d,l-trans-3-mercapto-4-(N-allyloxycarbonyl)aminotetrahydrofuran

Dissolve the triphenylmethylsulfide made in Example 12 (1.24 g) in MeOH (15 mL) and silver nitrate (493 mgs) and add 250 μl of pyridine dissolved in 5 ml of methanol. The silver mercaptide is quite soluble in methanol so remove the solvent under high vacuum and redissolve in acetonitrile (25 mL). Bubble hydrogen sulfide gas through the solution to immediately form silver sulfide (Ag₂S). Remove the solids by filtration through Celite and concentrate the filtrate under vacuum in order to remove dissolved excess H₂S. Use the resulting concentrated title compound in the following step without further purification.

EXAMPLE 14 allyl-(5R,6S,8R)-6-(1-hydroxyethyl)-2-[(trans-tetrahydro-3'-(N-allyloxycarbonyl)amino-4'-furanyl)thio]-penem-3-carboxylate Add a solution of 4-(N-allyloxycarbonyl)amino-3-mercapto-tetrahydrofuran made in Example 13 (2.78 mmoles) in acetonitrile (10 mL) to a solution containing sodium bicarbonate (250 mgs) acetonitrile (3 mL) and water (1.5 mL). Add to this biphasic mixture 450 mg of penem sulfoxide (compound 6) in 5 ml acetonitrile. Stir the biphasic mixture rapidly at room temperature for 15 min., dilute with brine (20 mL) and extract the product into ethylacetate (30 mL). Wash the organic layer with brine (2×20 mL) and dry (MgSO₄). Preparative TLC compound.

MS, M+/z=439.

EXAMPLE 15

(5R,6S,8R)-6-(1-hydroxyethyl)-2-[(trans-tetrahydro-3'-amino-4'-furanyl)thio]-penem-3-carboxylic acid To dry, oxygen free THF (10 mL), add palladium acetate (17.5 mgs) followed by triisopropylphosphite (154 mgs) in 2 mL THF and then 2-ethylhexanoic acid (163 mgs) and the penem allyl ester made in Example 14 (222.7 mgs) in 2 mL of THF. Stir the reaction under nitrogen for one hour. Add diethylether (25 mL) and collect the precipitate by centrifugation. Decant the solvent and wash the residue several times with diethylether and ethylacetate. Dry the residue under vacuum to give the title compound.

The following trans compounds of this invention can be made following the procedures of Examples 10-15, but in Example 10, a lower alkoxide is used in place of allyl alcohol, as shown in Table 3, then Examples 11, 12, 13, 14 and 15 are followed for compounds 7 and 8 and Examples 12, 13, 14 and 15 are followed for compound 9:

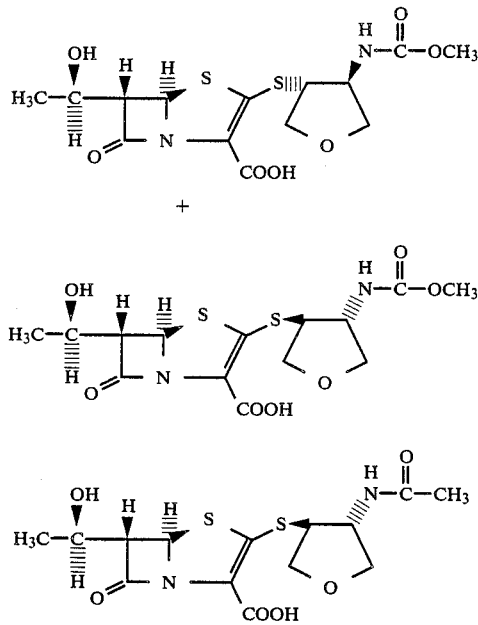

TABLE 3

| Starting Compound | Reaction | Product |
|---|---|---|
| 7. (I, NCO, tetrahydrofuran) | lower alkoxide | (I, NH-C(=O)-OCH₃, tetrahydrofuran) |
| 8. (I, NCO, tetrahydrofuran) | | (I, NH-C(=O)-OCH₃, tetrahydrofuran) |

TABLE 3-continued

| Starting Compound | Reaction | Product |
|---|---|---|
| 9. (I, NCO, tetrahydrofuran) | (1) H⁺ (2) OH⁻ acetyl chloride | (N-C(=O)-CH₃, tetrahydrofuran) |

[Hassner et al J. Org. Chem. 32 540 (1967)]

EXAMPLE 16

N-allyloxycarbonyl-3-pyrroline

To a solution of 3-pyrroline (3.5 gms) in ethanol (20 mL) was added ~25 mL saturated aq. NaHCO₃ and enough water to allow rapid stirring. The mixture was cooled to 10° C. and allyl chloroformate (5.92 mL) was slowly added via pressure equalized addition funnel. The mixture was removed from ice bath and allowed to stir at room temperature for 2 hours. Product was extracted into Et₂O (3×150 mL). The organic phase was washed with water (2×50 mL), dried (MgSO₄) and solvent was evaporated at reduced pressure. Purification on silica (Et₂O) afforded pure title compound.

MS, M+/z=154, H NMR (CDCl₃): δ 6.5-5.75 (m, 1H), δ 5.8 (s, 2H), 5.02-5.5 (m, 2H), 4.6 (dm, 2H, J=6.5 Hz), 4.20 (s, 4H).

EXAMPLE 17

N-allyloxycarbonyl-trans-3-bromo-4-hydroxypyrroline and N-allyloxycarbonyl-3-pyrroline-3,4-oxide To a cold (0° C.) solution of N-allyloxycarbonyl-3-pyrroline (9.7 gms) in 200 mL of 20% water in THF, was added 15.0 gms (1.15 eq.) of N-Bromosuccinimide. The mixture was removed from ice bath and allowed to stand at room temperature for ~1 hour. Then water was added (100 mL) followed by the addition of 25 mL of 10% NaHSO₃ (aq.) and the resulting mixture was stirred for 30 minutes. Finally, the pH was adjusted to 8.0-8.5 with 1M NaOH and stirring was continued for an additional 30 minutes. The product was extracted into EtOAc (2×200 mL) and the organic phase was washed with brine (1×100 mL), dried (MgSO₄) and solvent was evaporated under reduced pressure. Chromatography on silica gel (Et₂O/Hexane, 7:3) afforded the title compound.

MS, M+/z=170, H'NMR (CDCl₃): δ 5.7-6.15 (m, 1H), 5.1-5.4 (m, 2H) 4.55 (d, 2H, J=3 Hz), 3.85 (dd, 2H, J=10, 2 Hz), 3.7 (s, 2H), 3.35 (d, 2H, J=10 Hz).

EXAMPLE 18

N-allyloxycarbonyl-trans-3-hydroxy-4-triphenylmethylthio pyrroline

The compound prepared in Example 17 (870 mgs) was dissolved in 2 mL of dry DMF and cooled in an ice bath. To this was added a solution of sodium triphenyl methy ("trityl") thiolate, prepared by reacting 1.42 gms of tritylthiol with 125 mgs of sodium hydride in 10 mL of dry DMF. The mixture was allowed to stir under a nitrogen atmosphere overnight. Water (25 mL) was cautiously added and product was extracted into ether (3×30 mL). The ether layer was washed with water (2×10 mL) and dried (MgSO₄). Evaporation of solvent under vacuum and chromatography on silica gel afforded the title compound.

MS, M+/z 445, H'NMR (CDCl₃): δ 7.8–7.1 (m, 15H), 5.9 (m, 1H), 5.2 (m, 2H), 4.5 (br.d, 2H, J=6 Hz), 3.0–3.8 (br.m, 5H), 2.75 (bm, 1H), 1.7 (brm, 1H, D₂O exchanged).

EXAMPLE 19

N-allyloxycarbonyl-trans-3-hydroxy-4-mercapto pyrroline and allyl-(5R,6S,8R)-6-(1-hydroxyethyl)-2-[(N-allyloxy-carbonyl-trans-3'-hydroxy-4'-pyrrolinyl)thio]-penem-3-carboxylate To a solution of the compound prepared in Example 18 (660 mgs) in 6 mL of methanol, was added a solution of silver nitrate (250 mgs) in 6 mL of methanol and 150 mgs of pyridine. Precipitation of the organic silver salt occurred over 15 minutes and then solvent was decanted. The residue was washed several times with methanol and then dried under oil pump vacuum for several hours. A suspension of the silver salt in 7 mL of acetonitrile was treated with a solution of excess H₂S in acetonitrile (25 mL). The precipitated silver sulfide was removed by filtration through celite and solvent was evaporated with warming (45° C.) under reduced pressure. The residue was redissolved in acetonitrile (10 mL) and penem sulfoxide (compound 6) (250 mgs) was added. The mixture was cooled in an ice bath with stirring before adding a solution of sodium bicarbonate (0.20 gms) in 7 mL of water. The mixture was stirred under nitrogen for 15 minutes. Brine was added (15 mL) and the product was extracted into ethylacetate (2×30 mL). The organic layer was dried (MgSO₄) and solvent was evaporated to give a yellowish oil. Purification by chromatography on silica gel (30% acetate, CH₂Cl₂) gave the title compound.

MS, M+/z=456, H'NMR, (CDCl₃): 6.1–5.7 (m, 2H), 5.52–5.0 (m, 2H), 4.8–4.5 (m, 2H), 4.4–3.3 (m, 15H), 1.36 (d, 3H, J=7 Hz).

The following derivatized compounds of this invention can be made following the procedures of Examples 16–19, but after Example 18 the hydroxy group is derivatized as in Table I:

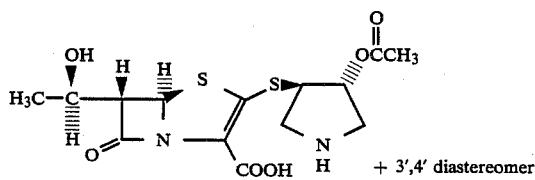
9.

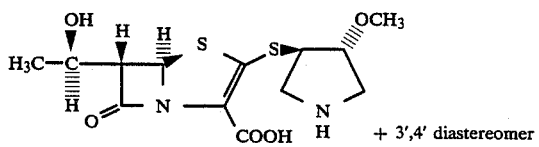
10.

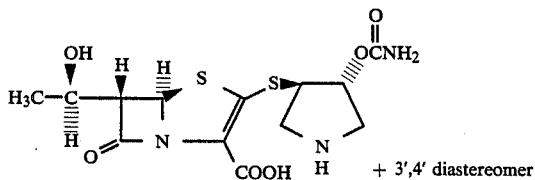
11.

EXAMPLE 20

3-hydroxy-4-triphenylmethylthio sulfolane

To a solution of 3-hydroxy-4-chloro sulfolane (1.7 gms) in 20 mL of DMF, was added a solution of sodium trityl thiolate (3.0 gms) in 20 mL of DMF. The mixture was kept under a nitrogen atmosphere for two hours. The mixture was diluted with water (100 mL) and product was extracted into ether (2×75 mL). The ether layer was washed with water (2×50 mL), dried (MgSO₄) and solvent ws evaporated under vacuum. The residue was purified by silica gel chromatography (100% CH₂Cl₂) and crystallized from ether/hexane to give the title compound as a solid.

MS, M+/z=378, H'NMR (DMSO-d₆): 7.6–7.1 (m, 15H), 6.1 (d, 1H, J=6 HZ), 4.20 (m, 1H), 3.5–2.3 (br.m, 4H), 2.1 (dd, 1H, J=15, 10 Hz).

EXAMPLE 21 allyl-(5R,6S,8R)-6-(1-hydroxyethyl)-2-[(3'-hydroxy-4'-sulfolanyl)thio]-penem-3-carboxylate To a solution of the 3-hydroxy-4-tritylthio sulfolane (1.0 gm) (in methanol (15 mL) was added a solution of silver nitrate (0.5 gms) and pyridine (0.25 mL) in 5 mL of methanol. Precipitation of the organic silver salt occurred immediately and after 15 minutes the solvent was decanted and discarded. The residue was washed with methanol (2×10 mL), and dried under vacuum (oil pump) for several hours. The residue was resuspended in acetonitrile (10 mL), a solution of excess H₂S in acetonitrile (25 mL). The mixture was stirred rapidly for 30 minutes under a nitrogen atmosphere and the black silver sulfide precipitate was removed by filtration through celite. Solvent was evaporated under reduced pressure and the residue was redissolved in acetonitrile. The mixture was cooled in an ice bath before adding a suspension of NaHCO₃ (250 mgs) in water (5 mL). The mixture was stirred under a nitrogen atmosphere for 15 minutes. Brine was added (15 mL) and the product was extracted into ethylacetate (2×25 mL). The organic layer was washed with brine (1×30 mL), dried (MgSO₄) and solvent was evaporated to give a yellowish oil. Purification by chromatography on silica gel (30% acetane/CH₂Cl₂) afforded the title compound.

MS, M+/z, 421; H'NMR (CDCl₃). δ 5.95 (m, 1H), 5.8 (d, 1H, J=1.5 Hz), 5.45 (d, 1H, J=15 Hz), 5.20 (d, 1H, J=10 Hz), 4.8–4.5 (dd, m, 2H, J=15, 6 Hz), 4.25–3.7 (m, 3H), 3.62 (dd, 1H, J=13, 6 Hz), 3.3 (ddm, 1H, J=13, 6 Hz), 3.15 (dd, 1H, J=13, 6 Hz), 1.27 (d, 3H, J=6.5 Hz).

In the following formulation examples "Drug" means Sodium (5R,6S,8R)-6-(1-hydroxyethyl)-2-[(cis-3'(R)-hydroxy-4'(S)-furanyl)thio]-penem-3-carboxylate or equivalent amounts of a compound of formula I.

EXAMPLE 22

Capsule Formula

| No. | Ingredient | mg/capsule | | |
|---|---|---|---|---|
| 1 | Drug | 100 | 250 | 50 |
| 2 | Lactose | 123 | 185 | 123 |
| 3 | Corn Starch | 50 | 60 | 70 |
| 4 | Magnesium Stearate | 2 | 5 | 7 |
| | Total | 275 | 500 | 700 |

Method of Manufacture

Mix Item Nos. 1, 2 and 3 in a suitable mixer for 10-15 minutes. Add Item No. 4 and mix for 1-3 minutes. Fill the mixture into suitable two-piece hard gelatin capsules using suitable encapsulating equipment.

EXAMPLE 23

Tablet Formula

| No. | Ingredient | mg/tablet | | |
|---|---|---|---|---|
| 1 | Drug | 100 | 250 | 500 |
| 2 | Lactose | 194.5 | 187.5 | 156.5 |
| 3 | Corn Starch, as a 10% paste | 5 | 10 | 15 |
| 4 | Corn Starch | 25 | 50 | 75 |
| 5 | Magnesium Stearate | 0.5 | 2.5 | 3.5 |
| | Total | 325 | 500 | 750 |

Method of Manufacture

Mix Items Nos. 1, 2 and a portion of Item No. 4 in a suitable mixer for 10-15 minutes. Granulate the mixture with Item No. 3. Pass the wet granulation through a coarse screen (e.g., ¼″) if needed, and then dry the wet granules. Mill the dried granules. Combine Item No. 5 and the remaining portion of Item No. 4 with the dried granules in a suitable blender and mix for 5-10 minutes. Compress the mixture to appropriate tablet size and weight on a suitable tablet machine.

EXAMPLE 24

Injectable Powder

| No. | Ingredient | mg/ml |
|---|---|---|
| 1 | Drug | 0.5-1.0 |
| 2 | Sodium Phosphate Monobasic | 2.0 (0.8-5.0) |
| 3 | Sodium Phosphate Dibasic | 1.0 (0-3.0) |
| 4 | Mannitol | 5.0 (1.0-10.0) |
| 5 | Water for Injection q.s. ad | 10. ml |

Method of Manufacture

Dissolve Items 1-4 in Item 5. Filter the resultant solution through a 0.22 μm membrane filter. Fill filtered solutions into prewashed and presterilized vials, and load them into a freeze-dryer. The solution is frozen and then vacuum-dried in the frozen state.

EXAMPLE 25

Injectable Solution

| No. | Ingredient | mg/ml |
|---|---|---|
| 1 | Drug | 0.5-1.0 |
| 2 | Sodium Phosphate Monobasic | 2.0 (0.8-5.0) |
| 3 | Sodium Phosphate Dibasic | 1.0 (0-3.0) |
| 4 | Ascorbic Acid | 0.05 (0.01-0.1) |
| 5 | Phenol | 0.4 (0.25-0.5) |
| 6 | Disodium Edetate | 0.03 (0.01-0.05) |
| 7 | Water for Injection q.s. ad | 1.0 ml |

Method of Manufacture

The injectable solution is manufactured by dissolving Items 1-6 in Item 7. Sterile filter the resultant solution through a 0.22μ membrane filter.

EXAMPLE 26

| Topical Cream | mg/g |
|---|---|
| Drug | 100.0 |
| Cetyl alcohol | 40.0 |
| Stearyl alcohol | 40.0 |
| Isopropyl myristate | 100.0 |
| Polyoxyethylene (2) monostearyl ether (Brij 72) | 10.0 |
| Polyoxyethylene (20) monostearyl ether (Brij 78) | 25.0 |
| Propylene glycol | 100.0 |
| Benzyl alcohol | 10.0 |
| Purified water q.s. ad | 1.0 g |

Method of Manufacture

Melt together and heat to about 70° the cetyl alcohol, stearyl alcohol, Brij 72, Brij 78 and isopropyl myristate. Add the propylene glycol to water in a separate container, heat to 70° C., and dissolve in this aqueous phase the benzyl alcohol. Dissolve or suspend the Drug in the aqueous phase while stirring. Add the aqueous phase to the oily phase with agitation. Start cooling and continue to agitate until the temperature reaches 25° C.

EXAMPLE 27

| Gel | mg/g |
|---|---|
| Drug | 200.0 |
| Propylene glycol | 100.0 |
| Hydroxypropylcellulose | 25.0 |
| Ethyl alcohol q.s. ad | 1.0 g |

Method of Manufacture

Disperse or dissolve the drug alcohol with agitation. Add the propylene glycol and then the hydroxypropylcellulose, maintaining agitation until the hydroxypropylcellulose is evenly dispersed. Cool the resulting gel to allow for completion of hydration.

EXAMPLE 28

| Topical Lotion | mg/g |
|---|---|
| Drug | 250.0 |
| Ethyl alcohol | 300.0 |
| Polyethylene glycol 400 | 300.0 |
| Hydroxypropylcellulose | 5.0 |
| Propylene glycol q.s. ad | 1.0 g |

Method of Manufacture

Dissolve or disperse the drug in the solvent mixture of ethyl alcohol, polyethylene glycol 400 and propylene glycol with agitation. Then add the hydroxypropylcellulose maintaining agitation, until the hydroxypropylcellulose is evenly dispersed.

We claim:

1. A compound represented by the formula:

and pharmaceutically acceptable salts or pharmaceutically acceptable esters thereof,
wherein:
X represents oxygen, or

wherein R is hydrogen, loweralkyl, acetyl or methoxycarbonyl;
Y is cis, trans or mixtures thereof and is selected from hydroxy, lower alkoxy, amino, carbamoyloxy, methoxycarbonylamino, lower alkylcarbonyloxy, lower alkylcarbonylamino and loweralkylsulfonylamino; and
the wavy lines indicate cis, trans or mixtures thereof.

2. A compound of claim 1 which is (5R,6S,8R)-6-(1-hydroxyethyl)-2-[(tetrahydro-3'-hydroxy-4'-furanyl)thio]-penem-3-carboxylic acid.

3. A compound of claim 2 which is the cis,3'R,4'S stereoisomer, i.e. (5R,6S,8R)-6-(1-hydroxyethyl)-2-[(tetrahydro-cis-3'(R)-hydroxy-4'(S)-furanyl)thio]-penem-3-carboxylic acid.

4. A compound of claim 2 which is the cis,3'S,4'R stereoisomer, i.e. (5R,6S,8R)-6-(1-hydroxyethyl)-2-[(tetrahydro-cis-3'(S)-hydroxy-4'(R)-furanyl)thio]-penem-3-carboxylic acid.

5. A compound of claim 1 which is the trans,3'R,4'R stereoisomer, i.e. (5R,6S,8R)-6-(1-hydroxyethyl)-2-[(tetrahydro-trans-3'(R)-hydroxy-4'(R)-furanyl)thio]-penem-3-carboxylic acid.

6. A compound of claim 2 which is the trans,3'S,4'S stereoisomer, i.e. (5R,6S,8R)-6-(1-hydroxyethyl)-2-[(tetrahydro-trans-3'(S)-hydroxy-4'(S)-furanyl)thio]-penem-3-carboxylic acid.

7. A compound of claim 1 which is (5R,6S,8R)-6-(1-hydroxyethyl)-2-[(tetrahydro-3'-methoxy-4'-furanyl)thio]-penem-3-carboxylic acid.

8. A compound of claim 7 which is the trans,3'R,4'R stereoisomer, i.e. (5R,6S,8R)-6-(1-hydroxyethyl)-2-[(trans-tetrahydro-3'(R)-methoxy-4'(R)-furanyl)thio]-penem-3-carboxylic acid.

9. A compound of claim 7 which is the trans,3'S,4'S stereoisomer, i.e. (5R,6S,8R)-6-(1-hydroxyethyl)-2-[(trans-tetrahydro-3'(S)-methoxy-4'(R)-furanyl)thio]-penem-3-carboxylic acid.

10. A compound of claim 1 which is (5R,6S,8R)-6-(1-hydroxyethyl)-2-[(tetrahydro-3'-acetoxy-4'-furanyl)thio]-penem-3-carboxylic acid.

11. A compound of claim 10 which is the trans,3'R,4'R stereoisomer, i.e. (5R,6S,8R)-6-(1-hydroxyethyl)-2-[(trans-tetrahydro-3'(R)-acetoxy-4'(R)-furanyl)thio]-penem-3-carboxylic acid.

12. A compound of claim 10 which is the trans,3'S,4'S stereoisomer, i.e. (5R,6S,8R)-6-(1-hydroxyethyl)-2-[(trans-tetrahydro-3'(S)-acetoxy-4'(S)-furanyl)thio]-penem-3-carboxylic acid.

13. A compound of claim 1 which is (5R,6S,8R)-6-(1-hydroxyethyl)-2-[(tetrahydro-3'-carbamoyloxy-4'-furanyl)thio]-penem-3-carboxylic acid.

14. A compound of claim 13 which is the trans3'R,4'R stereoisomer, i.e. (5R,6S,8R)-6-(1-hydroxyethyl)-2-[trans-tetrahydro-3'(R)-carbamoyloxy-4'(R)-furanyl)thio]-penem-3-carboxylic acid.

15. A compound of claim 13 which is the trans3'S,4'S stereoisomer, i.e. (5R,6S,8R)-6-(1-hydroxyethyl)-2-[(trans-tetrahydro-3'(S)-carbamoyloxy-4'(S)-furanyl)-thio]-penem-3-carboxylic acid.

16. A compound of claim 1 which is (5R,6S,8R)-6-(1-hydroxyethyl)-2-[(tetrahydro-3'-amino-4-furanyl)thio]-penem-3-carboxylic acid.

17. A compound of claims 16 which is the trans,3'R,4'R stereoisomer, i.e. (5R,6S,8R)-6-(1-hydroxyethyl)-2-[(trans-tetrahydro-3(R)-amino-4'(R)-furanyl)-thio]-penem-3-carboxylic acid.

18. A compound of claim 16 which is the trans,3'S,4'S stereoisomer, i.e. (5R,6S,8R)-6-(1-hydroxyethyl)-2-[(trans-tetrahydro-3'(S)-amino-4'(S)-furanyl)thio]-penem-3-carboxylic acid.

19. A compound of claim 16 which the cis,3'R,4'S stereoisomer, i.e. (5R,6S,8R)-6-(1-hydroxyethyl)2-[(cis-tetrahydro-3'(R)-amino-4'(S)-furanyl)thio]-penem-3-carboxylic acid.

20. A compound of claim 16 which is the cis,3'S,4'R stereoisomer, i.e. (5R,6S,8R)-6-(1-hydroxyethyl)-2-[(cis,tetrahydro-3'(S)-amino-4'(R)-furanyl)thio]-penem-3-carboxylic acid.

21. A compound of claim 1 which is sodium (5R,6S,8R)-6-[(1-hydroxyethyl)-2-[(tetrahydro-3'-methoxycarbonylamino-4'-furanyl)thio]-penem-3-carboxylate.

22. A compound of claim 21 which is the trans,3'S,4'S stereoisomer.

23. A compound of claim 21 which is the trans,3'R,4'R stereoisomer.

24. A compound of claim 1 which is (5R,6S,8R)-6-(1-hydroxyethyl)-2-[(3'-hydroxy-4'-pyrrolidinyl)thio]-penem-3-carboxylic acid.

25. A compound of claim 24 which is the trans,3'R,4'R stereoisomer.

26. A compound of claim 24 which is the trans,3'S,4'S stereoisomer.

27. A compound of claim 1 which is (5R,6S,8R)-6-(1-hydroxyethyl)-2-[(1'-acetyl-3'-hydroxy-4'-pyrrolidinyl)-thio]-penem-3-carboxylic acid.

28. A compound of claim 27 which is the trans,3'R,4'R stereoisomer.

29. A compound of claim 27 which is the trans,3'S,4'S stereoisomer.

* * * * *